(12) United States Patent
Olivier

(10) Patent No.: US 11,135,095 B2
(45) Date of Patent: Oct. 5, 2021

(54) TOE PROTECTION ASSEMBLY

(71) Applicant: David Olivier, Auburn, NH (US)

(72) Inventor: David Olivier, Auburn, NH (US)

( * ) Notice: Subject to any disclaimer, the term of this patent is extended or adjusted under 35 U.S.C. 154(b) by 260 days.

(21) Appl. No.: 16/437,170

(22) Filed: Jun. 11, 2019

(65) Prior Publication Data

US 2020/0390612 A1    Dec. 17, 2020

(51) Int. Cl.
*A61F 13/04* (2006.01)

(52) U.S. Cl.
CPC .................................. *A61F 13/041* (2013.01)

(58) Field of Classification Search
CPC .......... A61F 5/019; A61F 5/11; A61F 5/0111; A61F 5/14; A61F 2005/0132; A61F 2005/0181; A61F 13/068; A61F 5/0113; A61F 5/0127; A61F 13/064; A61F 13/063; A61F 5/0102; A61F 5/0125; A61F 13/06; A61F 2/4225; A61F 13/04; A61F 13/045
See application file for complete search history.

(56) References Cited

U.S. PATENT DOCUMENTS

| | | | |
|---|---|---|---|
| 3,609,888 A * | 10/1971 | Rickman | A43B 13/16 36/7.5 |
| 3,773,041 A | 11/1973 | Bogar | |
| 3,798,803 A | 3/1974 | Kennedy | |
| 3,832,997 A | 9/1974 | Cappelletti | |
| 4,061,138 A | 12/1977 | Bernstein | |
| 4,069,599 A * | 1/1978 | Alegria | A43B 3/20 36/106 |
| 4,263,902 A * | 4/1981 | Dieterich | A61F 5/019 601/27 |
| 4,454,872 A | 6/1984 | Brouhard | |
| 4,638,574 A * | 1/1987 | Roda | A43B 3/20 36/7.2 |
| 5,787,612 A * | 8/1998 | Mahoney | A63C 13/001 36/122 |
| 6,802,318 B1 | 10/2004 | Parker | |
| 9,579,231 B2 | 2/2017 | Galvin | |
| D793,678 S | 8/2017 | Burns | |

* cited by examiner

*Primary Examiner* — Ophelia A Hawthorne

(57) ABSTRACT

A toe protection assembly for inhibiting toes in a foot cast from being stubbed includes a basal strap that is positionable beneath a foot cast. A top strap is pivotally coupled to the basal strap such that the top strap can be extended over the foot cast when the basal strap is positioned beneath the foot cast. A ratchet strap is pivotally coupled to the basal strap such that the ratchet strap can be extended over the foot cast when the basal strap is positioned beneath the foot cast. A ratchet is coupled to the ratchet strap and the ratchet tightens the top strap across the foot cast. A barrier is coupled to the basal strap and the barrier extends across toes on a foot that is positioned in the foot cast. Moreover, the barrier is comprised of a rigid material to inhibit the toes from being stubbed during walking with the foot cast.

5 Claims, 4 Drawing Sheets

TOE PROTECTION ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relates to protection device and more particularly pertains to a new protection device for inhibiting toes in a foot cast from being stubbed.

BRIEF SUMMARY OF THE INVENTION

An embodiment of the disclosure meets the needs presented above by generally comprising a basal strap that is positionable beneath a foot cast. A top strap is pivotally coupled to the basal strap such that the top strap can be extended over the foot cast when the basal strap is positioned beneath the foot cast. A ratchet strap is pivotally coupled to the basal strap such that the ratchet strap can be extended over the foot cast when the basal strap is positioned beneath the foot cast. A ratchet is coupled to the ratchet strap and the ratchet tightens the top strap across the foot cast. A barrier is coupled to the basal strap and the barrier extends across toes on a foot that is positioned in the foot cast. Moreover, the barrier is comprised of a rigid material to inhibit the toes from being stubbed during walking with the foot cast.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
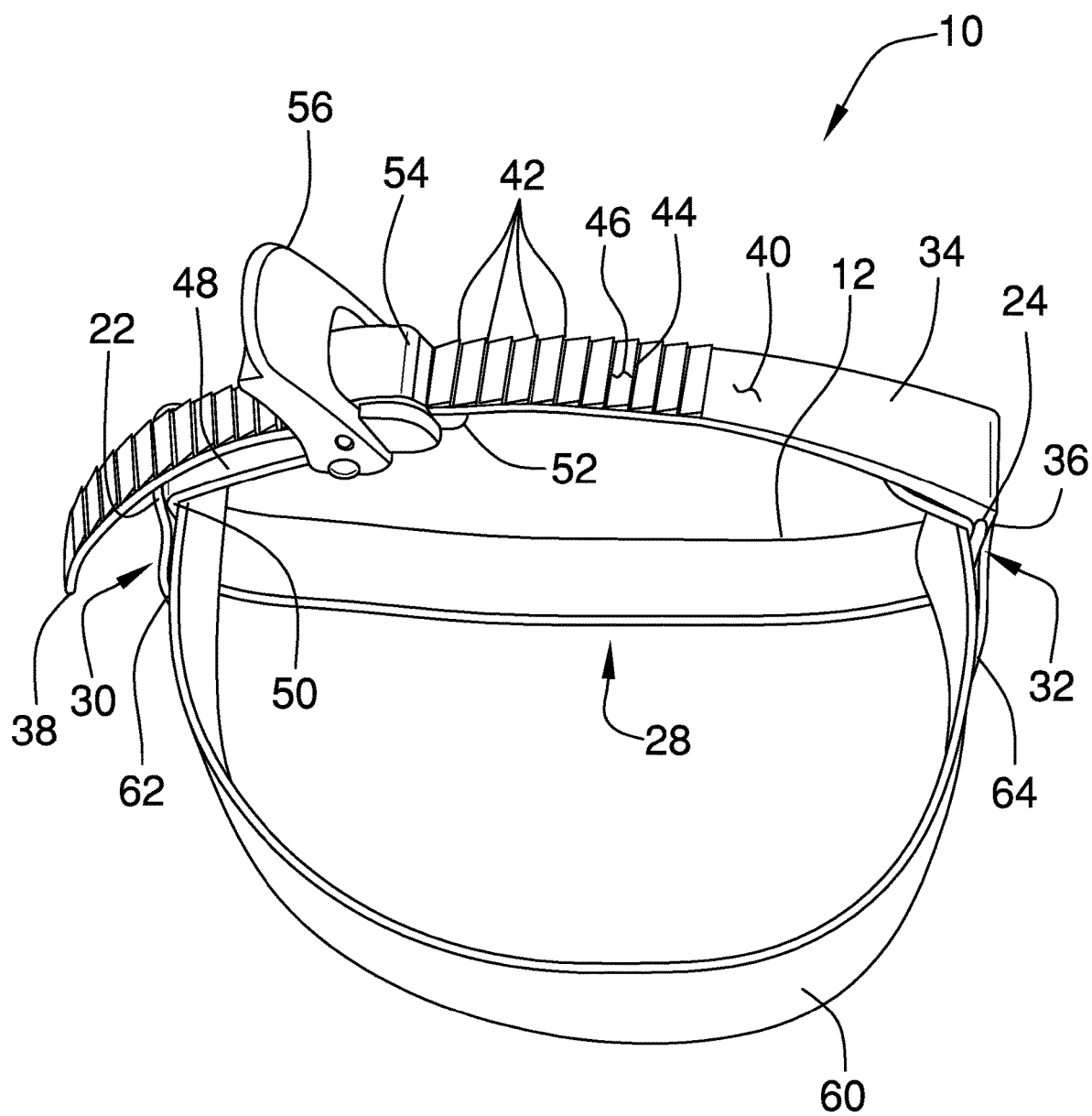
FIG. 1 is a perspective view of a toe protection assembly according to an embodiment of the disclosure.
Figure 2:
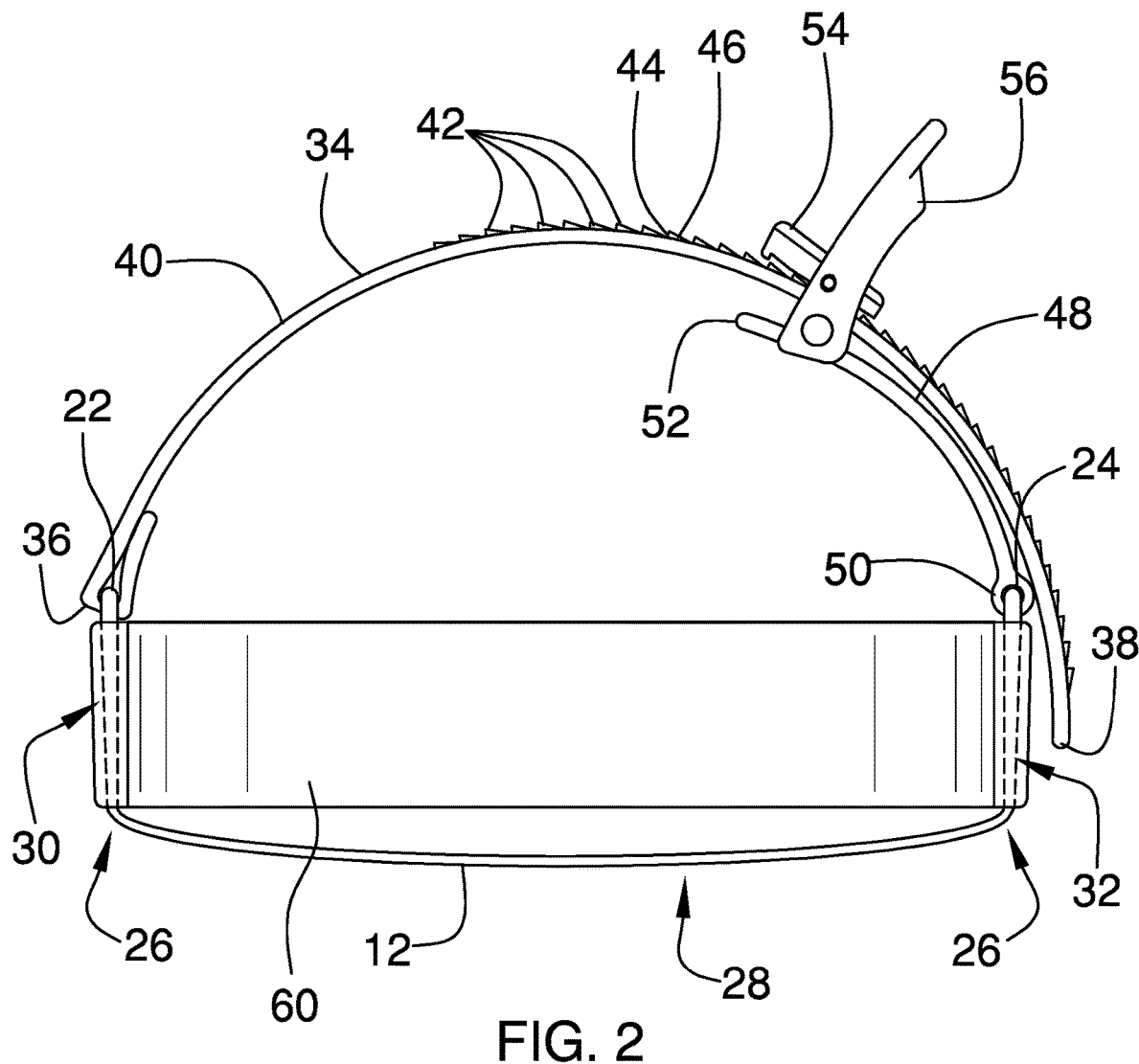
FIG. 2 is a front view of an embodiment of the disclosure.
Figure 3:
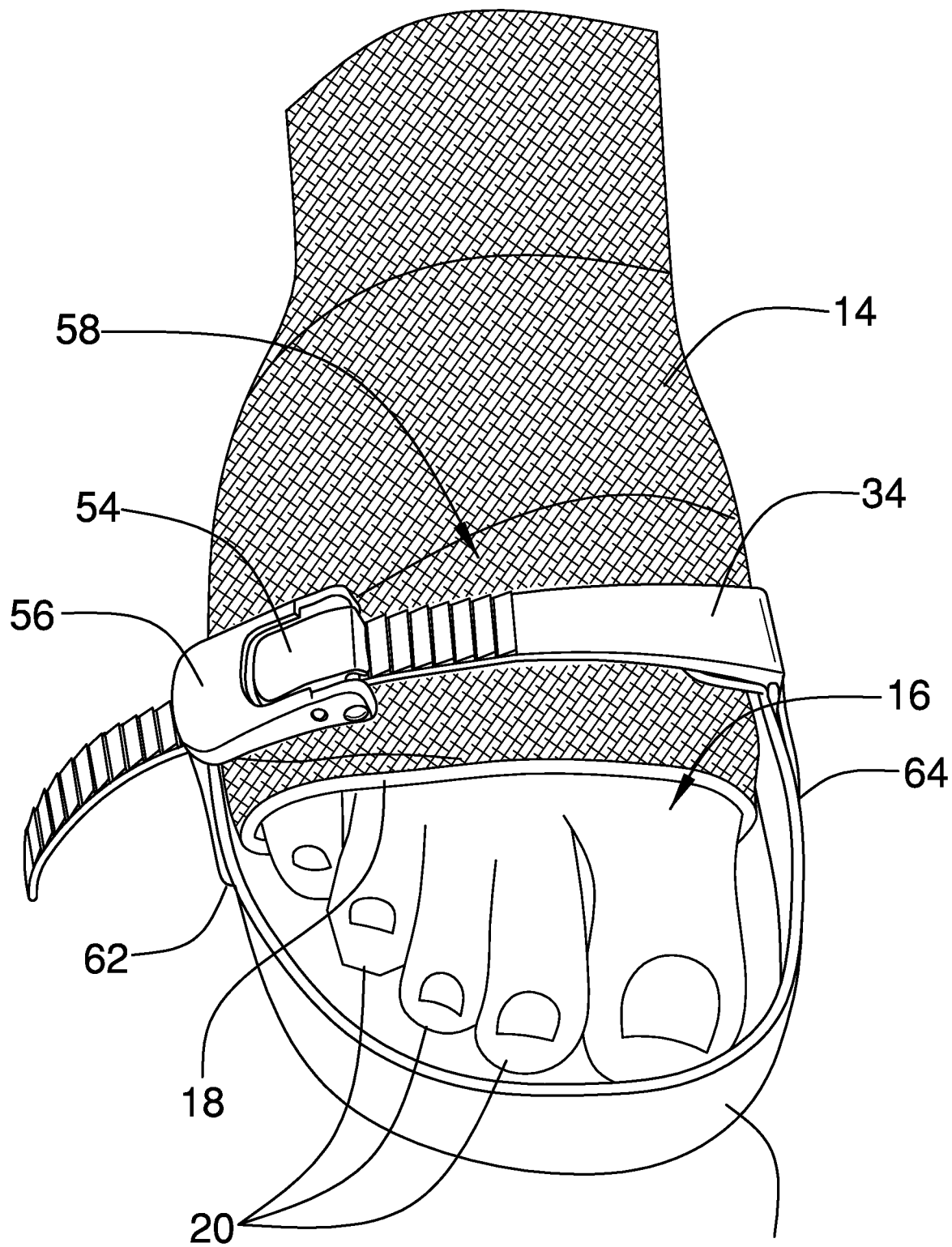
FIG. 3 is a perspective in-use view of an embodiment of the disclosure.
Figure 4:
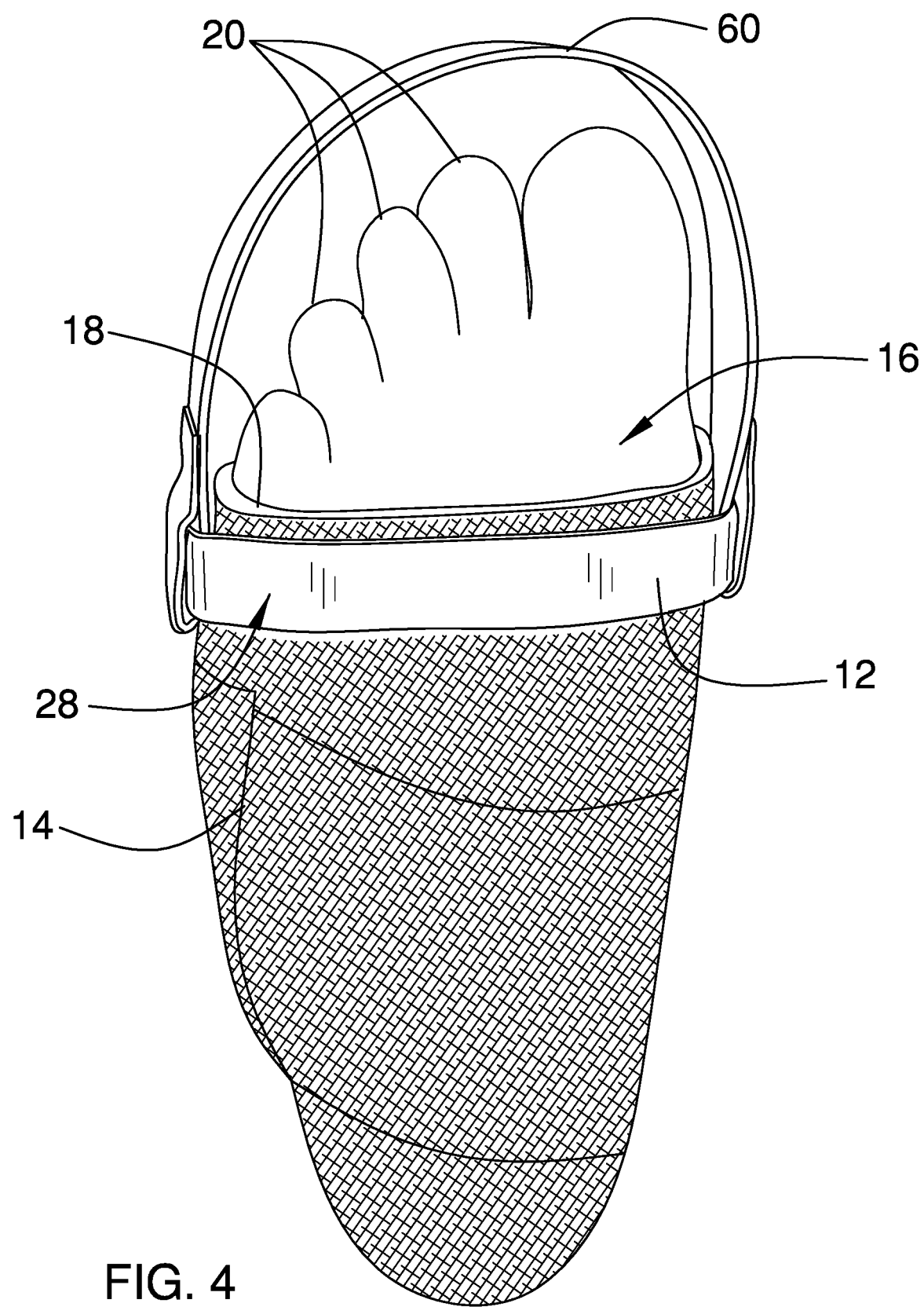
FIG. 4 is a bottom in-use view of an embodiment of the disclosure.

With reference now to the drawings, and in particular to FIGS. 1 through 4 thereof, a new protection device embodying the principles and concepts of an embodiment of the disclosure and generally designated by the reference numeral 10 will be described.

As best illustrated in FIGS. 1 through 4, the toe protection assembly 10 generally comprises a basal strap 12 that is positionable beneath a foot cast 14. The foot cast 14 may be a rigid foot cast that is worn on a person's foot 16 to facilitate healing of broken bones in the person's foot 16. Additionally, the foot cast 14 may have an open toe 18 through which toes 20 on the person's foot 16 extend. The basal strap 12 has a first end 22 and a second end 24. The basal strap 12 has a pair of bends 26 thereon to define a central portion 28 of the basal strap 12 extending between a first end portion 30 and a second end portion 32 of the basal strap 12. Each of the first 30 and second 32 end portions of the basal strap 12 extend upwardly along the foot cast 14 when the central portion 28 is positioned beneath the foot cast 14. Moreover, each of the first 30 and second 32 end portions has a respective one of the first 22 and second 24 ends being associated therewith.

A top strap 34 is provided and the top strap 34 is pivotally coupled to the basal strap 12. Thus, the top strap 34 can be extended over the foot cast 14 when the basal strap 12 is positioned beneath the foot cast 14. The top strap 34 has a primary end 36, a secondary end 38 and a top surface 40 extending therebetween. The primary end 36 is pivotally coupled to the first end 22 of the basal strap 12.

The top surface 40 has a plurality of ridges 42 extending upwardly therefrom. The ridges 42 are spaced apart from each other and are distributed from the secondary end 38 toward the primary end 36. Each of the ridges 42 has a front surface 44 extending upwardly from the top surface 40 of the top strap 34. Additionally, each of the ridges 42 has an upper surface 46 sloping downwardly from the front surface 44 to the top surface 40 of the top strap 34. The upper surface 46 of each of the ridges 42 terminates at the front surface 44 of an adjacent one of the ridges 42.

A ratchet strap 48 is provided and the ratchet strap 48 is pivotally coupled to the basal strap 12. Thus, the ratchet strap 48 can be extended over the foot cast 14 when the basal strap 12 is positioned beneath the foot cast 14. The ratchet strap 48 has a first end 50 and a second end 52, and the first end 50 of the ratchet strap 48 is pivotally coupled to the second 24 of the basal strap 12. A ratchet 54 is coupled to the ratchet strap 48. The ratchet 54 insertably receives the top strap 34 such that the basal strap 12, the top strap 34 and the ratchet strap 48 form a closed loop around the foot cast 14. Additionally, the ratchet 54 tightens the top strap 34 across the foot cast 14.

The ratchet 54 is positioned on the second end 52 of the ratchet strap 48 and the ratchet 54 includes a lever 56 that is pivotally coupled thereto. The lever 56 engages the front surface 44 of a respective one of the ridges 42 when the top strap 34 is extended through the ratchet 54. Additionally, the lever 56 urges the respective ridge 42 through the ratchet 54 when the lever 56 is manipulated for sequentially urging the ridges 42 through the ratchet 54. In this way the ratchet 54 tightens the top strap 34 and the ratchet strap 48 across the top 58 of the foot cast 14. The ratchet 54 is positionable in a releasing position for disengaging the top strap 34 to facilitate the top strap 34 to be removed from the ratchet 54.

A barrier 60 is coupled to the basal strap 12 and the barrier 60 extends across the toes 20 on the person's foot 16 that is positioned in the foot cast 14. The barrier 60 is comprised of a rigid material to inhibit the toes 20 from being stubbed during walking with the foot cast 14. The barrier 60 has a first end 62 and a second end 64, and the barrier 60 is elongated between the first 62 and second ends 64 of the barrier 60. The first end 62 of the barrier 60 is coupled to the first end portion 30 of the basal strap 12. The second end 64 of the barrier 60 is coupled to the second end portion 32 of the basal strap 12. Additionally, the barrier 60 is concavely arcuate between the first 62 and second 64 ends of the barrier 60. Each of the first 62 and second 64 ends of the barrier 60 may be wrapped around the respective first 30 and second 32 end portions of the basal strap 12.

In use, the central portion 28 of the basal strap 12 is positioned to extend laterally beneath the foot cast 14 having each of the first 30 and second 32 end portions of the basal strap 12 extending upwardly along opposite sides of the foot cast 14. Additionally, the basal strap 12 is positioned such that the barrier 60 is spaced from the toes 20 on the person's foot 16. The top strap 34 is extended through the ratchet 54 and the lever 56 on the ratchet 54 is manipulated to tighten the top strap 34 across the foot cast 14. In this way the barrier 60 is retained to extend in front of the toes 20 on the person's foot 16. Thus, the barrier 60 inhibits the toes 20 from being accidentally stubbed when the person walks in the foot cast 14.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A toe protection assembly being configured to be worn on a foot encased in a cast for protecting exposed toes on the foot from being struck on an object, said assembly comprising:
   a basal strap being positionable beneath a foot cast;
   a top strap being pivotally coupled to said basal strap such that said top strap can be extended over the foot cast when said basal strap is positioned beneath the foot cast;
   a ratchet strap being pivotally coupled to said basal strap such that said ratchet strap can be extended over the foot cast when said basal strap is positioned beneath the foot cast;
   a ratchet being coupled to said ratchet strap, said ratchet insertably receiving said top strap such that said basal strap, said top strap and said ratchet strap form a closed loop around the foot cast, said ratchet tightening said top strap across the foot cast; and
   a barrier being coupled to said basal strap wherein said barrier is configured to extend across toes on a foot that is positioned in the foot cast, said barrier being comprised of a rigid material wherein said barrier is configured to inhibit the toes from being stubbed during walking with the thot cast;
   wherein said basal strap has a first end and a second end, said basal strap having a pair of bends thereon to define a central portion of said basal strap extending between a first end portion and a second end portion of said basal strap, each of said first and second end portions of said basal strap extending upwardly along the foot cast when said central portion is positioned beneath the foot cast, each of said first and second end portions having a respective one of said first and second ends being associated therewith;
   wherein said top strap has a primary end, a secondary end and a top surface extending therebetween, said primary end being pivotally coupled to said first end of said basal strap; and
   wherein said top surface has a plurality of ridges extending upwardly therefrom, said ridges being spaced apart from each other and being distributed from said secondary end toward said primary end, each of said ridges having a front surface extending upwardly from said top surface of said top strap, each of said ridges having an upper surface sloping downwardly from said front surface to said top surface of said top strap, said upper surface of each of said ridges terminating at said front surface of an adjacent one of said ridges.

2. The assembly according to claim 1, wherein said ratchet strap has a first end and a second end, said first end of said ratchet strap being pivotally coupled to said second end of said basal strap.

3. The assembly according to claim 2, Wherein said ratchet is positioned on said second end of said ratchet strap, said ratchet including a lever being pivotally coupled thereto, said lever engaging said front surface of a respective one of said ridges when said top strap is extended through said ratchet, said lever urging said respective ridge through said ratchet when said lever is manipulated for sequentially urging said ridges through said ratchet, wherein said ratchet tightens said top strap and said ratchet strap across the top of the foot cast.

4. The assembly according to claim 1, wherein said barrier has a first end and a second end, said barrier being elongated between said first and second ends of said barrier, said first end of said barrier being coupled to said first end portion of said basal strap, said second end of said barrier being coupled to said second end portion of said basal strap, said barrier being concavely arcuate between said first and second ends of said barrier.

5. A toe protection assembly being configured to be worn on a foot encased in a cast for protecting exposed toes on the foot from being struck on an object, said assembly comprising:

a basal strap being positionable beneath a foot cast, said basal strap having a first end and a second end, said basal strap having a pair of bends thereon to define a central portion of said basal strap extending between a first end portion and a second end portion of said basal strap, each of said first and second end portions of said basal strap extending upwardly along the foot cast when said central portion is positioned beneath the foot cast, each of said first and second end portions having a respective one of said first and second ends being associated therewith;

a top strap being pivotally coupled to said basal strap such that said top strap can be extended over the foot cast when said basal strap is positioned beneath the foot cast, said top strap having a primary end, a secondary end and a top surface extending therebetween, said primary end being pivotally coupled to said first end of said basal strap, said top surface having a plurality of ridges extending upwardly therefrom, said ridges being spaced apart from each other and being distributed from said secondary end toward said primary end, each of said ridges having a front surface extending upwardly from said top surface of said top strap, each of said ridges having an upper surface sloping downwardly from said front surface to said top surface of said top strap, said upper surface of each of said ridges terminating at said front surface of an adjacent one of said ridges;

a ratchet strap being pivotally coupled to said basal strap such that said ratchet strap can be extended over the foot cast when said basal strap is positioned beneath the foot cast, said ratchet strap having a first end and a second end, said first end of said ratchet strap being pivotally coupled to said second of said basal strap;

a ratchet being coupled to said ratchet strap, said ratchet insertably receiving said top strap such that said basal strap, said top strap and said ratchet strap form a closed loop around the foot cast, said ratchet tightening said top strap across the foot cast, said ratchet being positioned on said second end of said ratchet strap, said ratchet including a lever being pivotally coupled thereto, said lever engaging said front surface of a respective one of said ridges when said top strap is extended through said ratchet, said lever urging said respective ridge through said ratchet when said lever is manipulated for sequentially urging said ridges through said ratchet, wherein said ratchet tightens said top strap and said ratchet strap across the top of the foot cast; and a barrier being coupled to said basal strap wherein said barrier is configured to extend across toes on a foot that is positioned in the foot cast, said barrier being comprised of a rigid material wherein said barrier is configured to inhibit the toes from being stubbed during walking with the foot cast, said barrier having a first end and a second end, said barrier being elongated between said first and second ends of said barrier, said first end of said barrier being coupled to said first end portion of said basal strap, said second end of said barrier being coupled to said second end portion of said basal strap, said barrier being concavely arcuate between said first and second ends of said barrier.

* * * * *